United States Patent [19]

Murtha et al.

[11] 4,177,164

[45] Dec. 4, 1979

[54] HYDROALKYLATION COMPOSITION AND PROCESS FOR PRODUCING SAID COMPOSITION

[75] Inventors: Timothy P. Murtha; William A. Jones; Ernest A. Zuech, all of Bartlesville, Okla.

[73] Assignee: Phillips Petroleum Company, Bartlesville, Okla.

[21] Appl. No.: 865,157

[22] Filed: Dec. 28, 1977

Related U.S. Application Data

[62] Division of Ser. No. 744,060, Nov. 22, 1976, Pat. No. 4,093,671.

[51] Int. Cl.$^2$ ............................................. B01J 29/06
[52] U.S. Cl. .................................................. 252/455 Z
[58] Field of Search ..................................... 252/455 Z

[56] References Cited

U.S. PATENT DOCUMENTS

| 3,173,854 | 3/1965 | Eastwood et al. | 252/455 Z |
| 3,210,265 | 10/1965 | Garwood | 252/455 Z |
| 3,534,115 | 10/1970 | Bushick | 252/455 Z |
| 3,546,100 | 12/1970 | Yan | 252/455 Z |
| 3,691,255 | 9/1972 | Takase et al. | 252/455 Z |
| 3,783,123 | 1/1974 | Young | 252/455 Z |
| 3,867,307 | 2/1975 | Scherzer et al. | 252/455 Z |

*Primary Examiner*—Carl Dees

[57] ABSTRACT

An aromatic hydrocarbon is contacted under hydroalkylation conditions and in the presence of hydrogen with a composition comprising at least one platinum compound supported on a calcined, acidic, nickel and rare earth-treated crystalline zeolite.

13 Claims, No Drawings

HYDROALKYLATION COMPOSITION AND PROCESS FOR PRODUCING SAID COMPOSITION

This is a division of application Ser. No. 744,060, filed Nov. 22, 1976, U.S. Pat. No. 4,093,671.

The invention relates to a hydroalkylation process, a composition useful as a catalyst in said process and a method for producing said composition.

Prior art catalysts in the field of hydroalkylation processes suffered from several drawbacks. These deficiencies of the prior art catalysts for the hydroalkylation reaction included: (1) The use of support materials for certain catalysts which are not able to withstand the temperatures employed in a typical air burn-off regeneration operation. Such regeneration operations are commonplace in the catalytic art for hydrocarbon conversions of various types and it is highly desirable that the catalyst for the hydroalkylation process be stable to such typically employed regeneration conditions. (2) Productivity is rather low as judged by the low liquid hourly space velocities (LHSV) that are utilized in the prior art. Thus a more active and more selective hydroalkylation catalyst is desired. (3) A number of the catalysts of the prior art for the hydroalkylation reaction are prepared by very complex and time consuming processes. For example, starting with a powdered crystalline zeolite support, said support is cation exchanged, washed and then incorporated into a matrix of another material such as silica-alumina. This combination is calcined, cooled, and impregnated with certain metal salts. Finally the composite is extruded into pellets and the like. Thus it is desirable that a more simplified and less expensive process for making active and selective catalysts be found. (4) Certain catalysts of the prior art for the hydroalkylation reaction were of fixed acidity because of the type of support material utilized. This left little variation that could be made in this important property of the hydroalkylation catalyst. It is therefore desirable that catalysts be developed which are varied easily in their acidity characteristics.

It is an object of the present invention to hydroalkylate aromatic compounds. Another object of the present invention is to provide a method for producing a composition useful as a hydroalkylation catalyst.

Another object of the invention is a composition useful as a catalyst in hydroalkylation reactions which is regenerated by air burn-off.

Another object of the invention is a composition useful as a catalyst in hydroalkylation reactions which is more active and more selective than prior art catalysts.

Another object of the invention is a composition useful as a catalyst in hydroalkylation reactions which is simpler and less expensive to produce as compared to prior art catalysts.

Still another object of the invention is a composition useful as a catalyst in hydroalkylation reactions in which the acidity of the catalyst can be adjusted.

SUMMARY

According to the invention an aromatic hydrocarbon is contacted under hydroalkylation conditions and in the presence of hydrogen with a composition comprising at least one platinum compound supported on a nickel and rare earth-treated crystalline zeolite support which is calcined to produce an acidic support before or after impregnating the platinum compound on the support. Such a composition when used as a catalyst is regenerated by air burn-off and is a highly active and selective catalyst.

Further according to the invention a composition comprises at least one platinum compound supported on a calcined, acidic, nickel and rare earth-treated crystalline zeolite.

Further according to the invention the above composition is prepared by contacting a crystalline zeolite with an aqueous cation exchange solution comprising rare earth, nickel and ammonium compounds; removing the zeolite from said solution and washing said zeolite with water to remove excess ions; calcining said cation exchanged zeolite; cooling said calcined zeolite; and impregnating said cation exchanged zeolite before or after said calcination step with a solution comprising at least one platinum compound in a suitable solvent and removing said solvent by evaporation. The acidity of the above composition is easily adjusted by varying the conditions under which the cation exchange step is carried out, such as, for example, adjusting the concentration of an ammonium compound in the cation exchange solution.

DETAILED DESCRIPTION OF THE INVENTION

The composition of the instant invention can be briefly described as a crystalline zeolite which has been cation exchanged with rare earth, nickel and ammonium compounds followed by a calcination step and a platinum compound impregnation step wherein the platinum compound can be impregnated on the cation exchanged zeolite to give the final composition either before or after the calcination step. Although not absolutely necessary, it is preferred that the above catalyst be treated with hydrogen prior to introduction of the aromatic hydrocarbon feed in the hydroalkylation process because of improved results.

The compositions of the instant invention are useful as catalysts and to some extent solve or obviate each of the above-mentioned deficiencies of the prior art catalyst. For example, the supports utilized for the compositions of the instant invention are stable to regeneration conditions utilized under typical air burn-off operations; they appear to operate at higher levels of productivity in that they show a higher degree of activity and selectivity than certain of the prior art catalysts; the process of making the compositions of the instant invention is simple and straightforward and the compositions thus obtained should be less expensive than those of the prior art which utilize very complex steps in their preparation; and the compositions of the instant invention can be made with a high degree of flexibility in the degree of acidity simply by adjusting the cation exchange conditions on the crystalline zeolite support utilized for the compositions of this invention.

The support material for the composition employed in the instant invention is a crystalline zeolite which has been treated under cation exchange conditions with a mixture of rare earth, nickel and ammonium compounds such that the cation metal content of the support is partially exchanged. Generally the cationic metal is an alkali metal which is sufficiently removed by cation exchange such that the remaining alkali metal content after the cation exchange step ranges from about 0.01 to about 2 percent by weight; however, the runs carried out in accordance with the invention and reported herein indicate that good results can be obtained when the alkali metal content of the cation exchanged zeolite ranges from about 0.1 to about 1 percent by weight. Some of the more commonly employed crystalline zeolites which are suitable for use in accordance with the present invention are the Type X or Type Y crystalline zeolites which are sometimes called molecular sieves because of their essentially uniform pore diameters. Some suitable Type Y synthetic crystalline zeolites are described for example in U.S. Pat. No. 3,130,007 and some suitable Type X zeolites are described in U.S. Pat. No. 2,882,244. Such materials are presently commercially available as for example zeolites SK-40 (Type Y) and 13X (Type X) from the Linde Division of Union Carbide Corporation, New York, N.Y.

The alkali metal form of the crystalline zeolites usually comprises sodium as the alkali metal and said zeolites are treated under cation exchange conditions with a mixture of rare earth, nickel and ammonium compounds in accordance with the present invention in order to provide a suitable support material for use in the preparation of the compositions of the invention.

It is contemplated that any of the readily available rare earth metal compounds may be employed in the cation exchange solution. Generally, the compounds used are those in which the rare earth metal-containing ion is present in the cationic state. Representative rare earth metal compounds include nitrates, bromides, acetates, chlorides, iodides, sulfates and mixtures thereof of one or more of the rare earth metals including cerium, lanthanum, praseodymium, neodymium, samarium, europium, gadolinium, terbium, dysprosium, holmium, erbium, thulium, ytterbium, and lutetium. Compounds of the rare earths named above may be employed singly, however, it is often convenient to employ mixtures of the rare earths as these are commercially available. For example, mixtures of rare earth metal compounds such as the chlorides of lanthanum, cerium, praseodymium, neodymium, samarium and gadolinium are available commercially at a relatively low cost and may be effectively employed.

As noted above, the zeolite material is cation exchanged with a mixture of rare earth, nickel and ammonium compounds according to the instant invention. Any convenient ammonium compound may be employed although the chloride is preferred because it is inexpensive and readily available. The weight ratio of ammonium compound to nickel and rare earth compounds in the aqueous exchange solution can be selected over a broad range. Generally the weight ratio of ammonium compound to nickel and rare earth compounds combined is within the range of from about 0.05:1 to about 20:1, although the data contained herein indicates that a range of from about 0.2:1 to about 5:1 can be used with good results. The concentration of rare earth compounds in the aqueous exchange solution can be varied over a wide range and exchange conditions can be adjusted accordingly such that the rare earth content of the ion exchanged crystalline zeolite can be selected over a broad range. Generally, the content of the final catalyst composite in terms of the rare earth elements is from about 2 to about 25 weight percent. The runs described herein indicate that the rare earth content of the catalyst can be within the range of from 5 to 20 weight percent. Good results were obtained employing a rare earth content of about 10 percent by weight. As noted above, the alkali metal content, for example sodium, of the exchanged catalyst support is partially removed by the ion exchange step and the alkali metal is generally from about 0.01 to about 2 percent by weight; however, the runs described herein indicate that good results can be obtained employing an alkali metal content ranging from about 0.1 to about 1 percent by weight.

The nickel compounds which will be employed in admixture with the above-named rare earth metal compounds and ammonium compounds are those wherein the nickel ion is present in the cationic state. Some suitable compounds representative of the nickel compounds which can be used in the invention include the nitrates, bromides, acetates, chlorides, iodides, sulfates and mixtures thereof.

The nickel content in the final composition can also be selected over a broad range. Generally the composition will comprise from about 0.01 to about 15 weight percent nickel, although the runs carried out in accordance with the invention and described herein indicate that good results can be obtained employing a nickel content ranging from about 1 to about 8 percent by weight.

The procedure whereby the Type X and Type Y zeolites are treated with aqueous solutions of rare earth, nickel and ammonium compounds to replace a portion of the alkali metal content of the zeolite is a cation exchange process which can be carried out in a batch or continuous fashion. Generally the exchange process is carried out on a continuous basis under the following typical conditions. A fixed bed of the zeolite material is treated with said aqueous solution of the rare earth, nickel and ammonium compounds at a temperature of 90° to 110° C. under conditions such that from about 0.1 to about 0.5 of the volume of aqueous salts solution per volume of zeolite is in contact with said zeolite per hour or, in other words, an LHSV ranging from about 0.1 to about 0.5 is employed in the exchange process. Under these conditions, the exchange process can be completed in 48 hours or less to achieve the desired level of rare earth, nickel and ammonium ions in the zeolite. The exchanged zeolite is then washed free of excess ions from the exchange step with water. The excess wash water is removed by drying the zeolite at a temperature ranging from about 100° C. to about 300° C. just prior to calcination. The instant catalyst can be calcined before impregnation with the platinum compound to be described below or the impregnation can be carried out prior to the calcination step. In either case, the calcination is carried out by slowly heating the zeolite from about 100° to 200° C. to a temperature within the range of from about 200° to about 550° C. in order to calcine the zeolite and convert the ammonium cations to the hydrogen form. Usually, the calcination is conducted until a constant weight is obtained for the zeolitic material, generally from about 2 to about 10 hours. The calcined zeolite is then cooled in ambient air, i.e., under conditions of normal humidity.

The above described support is impregnated with a solution of at least one platinum compound followed by evaporation of the solvent used in the impregnation step. Evaporation of the solvent can be conducted under vacuum if desired. Suitable solvents include water, alcohols, such as ethanol, ketones, such as acetone, and the like. Some of the various platinum compounds that can be employed in the impregnation step are as follows: ammonium hexachloroplatinate(IV), ammonium tetrachloroplatinate(II), chloroplatinic acid, diaminoplatinum dinitrite, platinic acid, platinum tetrachloride and mixtures thereof. The impregnation is generally carried out under what may be called "total impregnation" whereby the entire solids in the solutions used in the impregnation are left on the catalyst support and the liquid solvent for said compounds is simply removed by evaporation.

The platinum content in the final composition can be selected over a broad range. Generally the platinum content ranges from 0.01 to about 1 percent by weight although the runs described herein indicate that good results can be obtained employing a platinum content within the range of from about 0.05 to 0.25 percent by weight.

The composition described above is employed for the hydroalkylation of aromatic hydrocarbons to produce cycloalkyl aromatic hydrocarbons. Some of the feedstocks which are suitable for use in the present invention are aromatic compounds, i.e., monocyclic aromatic hydrocarbons and alkyl-substituted monocyclic aromatic hydrocarbons. Some specific examples of these are benzene, toluene, xylenes, and the like, and mixtures thereof. The aromatic hydrocarbon feedstocks should be essentially free of sulfur-containing compounds and other known poisons for hydrogenation catalysts in general. However, it is believed that a small amount of water, e.g., 20–50 ppm, in the feedstock is beneficial for maintaining catalyst activity over an extended period, e.g., several days.

The invention is particularly valuable for the conversion of benzene to cyclohexylbenzene. Cyclohexylbenzene is known as a valuable solvent and chemical intermediate. It can be converted in high yield to phenol and cyclohexanone by auto-oxidation with subsequent acid treatment. It is also useful as an intermediate in the production of cyclohexene which in turn can be utilized for the production of adipic acid and caprolactam.

The aromatic hydrocarbon feedstock is fed to the catalyst in a reaction zone operated under a wide range of conditions. The feedstock liquid hourly space velocity (LHSV), reaction temperature and pressure, and the hydrogen feed rate are not particularly critical; however, the liquid hourly space velocity (LHSV) generally ranges from about 1 to about 100, the reaction pressure generally ranges from about 690 to about 13,800 kPa (about 100 to about 2,000 psig), the hydrogen feed rate generally ranging from about 0.2 to about 1 mole per mole of aromatic hydrocarbon feedstock per hour, and the reaction temperature generally ranging from about 100° to about 250° C. Based upon the runs described herein good results can be obtained employing a liquid hourly space velocity (LHSV) within the range of from about 5 to about 25, a reaction pressure within the range of from about 1,380 to about 6,900 kPa (about 200 to about 1,000 psig), the hydrogen feed rate within the range of from about 0.2 to about 1 mole per mole of aromatic hydrocarbon feed per hour, and the reaction temperature within the range of from about 140° to about 200° C.

The hydroalkylation reaction is conveniently carried out by having the above described catalyst in a fixed bed reactor and then contacting said catalyst with the aromatic hydrocarbon feed and hydrogen in an upflow or downflow arrangement. It is also possible to employ a countercurrent flow of hydrogen and the aromatic hydrocarbon feed over the catalyst in the reaction zone. It is also possible to carry out the hydroalkylation reaction under batch conditions although a batch process is less preferred, because it is normally more expensive to operate and initial equipment costs are higher based upon the same size process.

Although a fixed bed reactor is mentioned above, most any type of reaction zone can be used as the particular type of reaction zone is not believed to be a critical parameter of the invention.

The reaction mixture from the reaction zone can usually be conveniently separated into the desired components by simple fractional distillation, and recycle of the unreacted feedstock and unreacted hydrogen can be accomplished as desired. The hydroalkylation products can be further purified as desired after separation from unreacted feedstock.

It is generally desirable to pretreat the catalyst with hydrogen gas prior to contacting the catalyst with the aromatic hydrocarbon in order to prereduce the catalyst. Based upon the runs described hereinafter, the hydrogen pressure and feed rate for the pretreating step generally is the same as that to be employed when contacting the aromatic hydrocarbon with the catalyst. In the hydroalkylation runs of the examples hereinafter described, the catalyst in the reactor was first reduced at 150° C. for 15 minutes under 3,450 kPa (500 psig) hydrogen at a hydrogen flow rate of 0.32 liters per minute before benzene was introduced to the reactor. Hydrogen pressure during the hydroalkylation process was maintained at 3,450 kPa (500 psig) and at a flow rate of about 0.32 liters per minute.

EXAMPLE I

Catalyst Preparation

Two catalysts were prepared for use in hydroalkylation reactions according to the instant invention. One catalyst No. 1) employed a Type X crystalline zeolite as the support material while the other catalyst (No. 2) employed a Type Y zeolite as the support material.

In the preparation of catalyst No. 1 a glass tube of 45 millimeter diameter which was equipped with heating means and means for passing an aqueous solution of compounds therethrough was charged with 200 grams of a Type X crystalline zeolite (Davison 13X mole sieves of 8–12 mesh manufactured by Davison Chemical Division of W. R. Grace and Co., Baltimore, Md.). An aqueous solution of 400 grams of ammonium chloride, 100 grams of rare earth chlorides, and 200 grams of nickel chloride ($NiCl_2$) hexahydrate in 4 liters of deionized water was prepared. Said rare earth chlorides were utilized as a commercially available mixture from the American Potash Corporation of the following composition: $MCl_3.6H_2O$ wherein M equals lanthanum 23%, cerium 43.5%, praseodymium 5.4%, neodymium 17.9%, samarium 1.9%, gadolinium 0.6%, and others 0.2%. The crystalline zeolite material was first wetted with a portion of the above solution and then charged to the tubular glass reactor described above and the remainder of the aqueous solution pumped over the crystalline zeolite at an LHSV of about 0.25. The temperature in the cation exchange zone was about 100° C. After the solution had been pumped through the crystalline zeolite bed, the material was cooled, filtered and washed six times with 350 ml portions of water and then allowed to dry in ambient air. A portion (27.3 grams) of the cation-exchanged crystalline zeolite was then treated with a solution of 0.054 grams of chloroplatinic acid ($H_2PtCl_6$) hexahydrate in 25 ml of water under total impregnation conditions. The impregnated crystalline zeolite was dried under vacuum to give a weight of 26.2 grams of the zeolite material. This material was then calcined by heating for about four hours in a furnace to about 205° C. (400° F.) and then the temperature increased slowly up to about 524° C. (975° F.) over an 8 hour period and then allowed to cool in air. The catalyst thus prepared contained 0.1% platinum, 4.68% nickel, 9.5% rare earths, and 0.63% sodium by weight.

In a similar manner to that described above, 250 grams of a Type Y crystalline zeolite (Linde SK-40 of 14–20 mesh manufactured by the Linde Division, Union Carbide Corporation, New York, N.Y., was treated (for preparation of catalyst No. 2) under cation exchange conditions with 4 liters of the aqueous solution of ammonium chloride, rare earth chlorides and nickel chloride. A portion (38.5 grams) of the above described catalyst material was impregnated with 0.0796 grams of chloroplatinic acid hexahydrate in about 80 ml of absolute ethanol under total impregnation conditions. The ethanol was removed on a rotary evaporator and the resulting material calcined by heating in a furnace under conditions similar to that described in the preparation of catalyst No. 1 above. Analytical results indicated that catalyst No. 2 contained 0.1% platinum, 1.33% nickel and 1.56% sodium by weight. In this instance, no analysis for the rare earths was carried out but based on previous experience the rare earth metal content was estimated to be 12–13% by weight.

perature while excess water evaporated. A portion (30 grams) of the above described crystalline zeolite, which had been cation exchanged with the solution of ammonium chloride and rare earth chlorides, was impregnated with 0.0787 grams of chloroplatinic acid hexahydrate in 80 ml of absolute ethanol under total impregnation conditions. The ethanol was then removed on a rotary evaporator. The impregnated material (21.6 grams) was heated overnight from room temperature up to about 196° C. (385° F.) and then the temperature raised over an 8 hour period to 507° C. (945° F.) under calcination conditions. The catalyst material was allowed to cool and then was ready for utilization in benzene hydroalkylation runs. The catalyst (No. 3) contained 0.1% platinum, 16.37% rare earths and 0.65% sodium.

Catalyst No. 4 was prepared such that it contained no rare earths or platinum. In the preparation of this catalyst 200 grams of a Type X crystalline zeolite of the same type previously used for catalyst No. 3 was wetted with a portion of a solution of 400 grams of ammonium chloride and 200 grams of nickel chloride hexahydrate in 4 liters of distilled water and then charged to the cation exchange reactor described above. The remainder of the solution of ammonium chloride and nickel chloride was then pumped over the zeolite bed under conditions which were essentially the same as those Table I

| Run No. | Catalyst No. | Temp. °C. | Benzene LHSV | Benzene Conv. % | Selectivity, Wt. %$^{(a)}$ CH$^{(b)}$ | $C_{12}H_{22}$$^{(c)}$ | MCPB$^{(d)}$ | CHB$^{(e)}$ | Heavies$^{(f)}$ | Weight Ratio CHB/CH |
|---|---|---|---|---|---|---|---|---|---|---|
| 1 | 1 | 158 | 11 | 10.2 | 15.7 | 0.78 | 0.98 | 71.5 | 11.0 | 4.5 |
| 2 | 1 | 170 | 15.6 | 9.0 | 12.2 | 0.67 | 1.55 | 74.4 | 10.4 | 6.1 |
| 3 | 1 | 180 | 15.6 | 8.9 | 12.4 | 0.67 | 1.80 | 75.2 | 9.8 | 6.1 |
| 4 | 1 | 170 | 18.0 | 10.8 | 14.8 | 1.02 | 1.48 | 69.4 | 13.0 | 4.7$^{(g)}$ |
| 5 | 2 | 160 | 13 | 7.8 | 26.9 | 0.64 | 1.28 | 59.0 | 12.8 | 2.2 |

$^{(a)}$Analysis by gas-liquid phase chromatography (GLC) of reaction zone effluent.
$^{(b)}$CH = Cyclohexane.
$^{(c)}$$C_{12}H_{22}$ = Compounds of the indicated general formula including bicyclohexyl.
$^{(d)}$MCPB = Methylcyclopentylbenzenes.
$^{(e)}$CHB = Cyclohexylbenzene.
$^{(f)}$Heavies = Mixture of compounds greater than $C_{12}H_{22}$.
$^{(g)}$Run made after catalyst was regenerated by heating to 500° C. with flowing air at atmospheric pressure for three hours. Catalyst was cooled and then prereduced as before with hydrogen.

The above runs illustrate the operability of the invention with both Type X and Type Y crystalline zeolites; however, in this particular instance the Type X zeolite produced the higher conversion of benzene and selectivity to cyclohexylbenzene.

EXAMPLE II

Catalyst Preparation

Other catalysts were prepared which were outside the scope of the instant invention and these catalysts then utilized in benzene hydroalkylation runs.

Catalyst No. 3 was prepared such that no nickel was present as a catalyst component. In the preparation of this catalyst, 200 grams of a Type X crystalline zeolite (Davison 13X mole sieves) in the form of ⅛" diameter spheres was wetted with a solution of 400 grams of ammonium chloride and 200 grams of rare earth chlorides in 4 liters of water and then charged to the cation exchange reactor utilized in the cation exchange processes of Example I. The remainder of the 4 liters of the solution was pumped over the crystalline zeolite bed at an LHSV of about 0.25 at a temperature of about 95° to 100° C. The zeolite material was cooled, filtered and then washed six times with 350 ml portions of water. The zeolite material was allowed to stand at room temdescribed for Catalyst No. 3. The cation-exchange crystalline zeolite was cooled, filtered and washed as described above and allowed to dry in air overnight. The zeolite material was then calcined by heating overnight to about 218° C. (425° F.) and then increasing the temperature over an 8 hour period to 532° C. (990° F.) and then allowed to cool. This catalyst (No. 4) contained 7.7% nickel and 1.54% sodium.

Catalyst No. 5 was prepared such that it contained no platinum. This catalyst was in effect the calcined support material utilized for the preparation of catalyst No. 1 described in Example I. Thus, catalyst No. 5 contained 4.68% nickel, 9.5% rare earths and 0.63% sodium. Calcination of this support material was carried out under essentially the same conditions utilized in calcining catalyst No. 1.

Catalyst No. 6 was prepared such that is contained no rare earths. This catalyst was prepared by utilizing catalyst No. 4 described above as the support for an impregnation carried out with chloroplatinic acid. In this preparation, 20 grams of the catalyst No. 4 was impregnated with 0.055 grams of chloroplatinic acid hexahydrate in about 50 ml of absolute ethanol. The ethanol was removed under vacuum on a rotary evaporator and more ethanol added and then evaporated a second time. The catalyst was then ready for use in hydroalkylation reaction. This catalyst contained 0.1% platinum, 7.7% nickel and 1.54% sodium.

Benzene Hydroalkylation

The catalysts described above which are outside the scope of the instant invention were utilized for benzene hydroalkylation under conditions similar to those utilized in the runs of Example I. For example, hydrogen pressure at 3,450 kPa (500 psig) and at a flow rate of 0.32 liters per minute was utilized in the runs with these catalysts. Other reaction conditions as well as the results obtained in the benzene hydroalkylation runs are shown below in Table II.

Table II

| Run No. | Catalyst No. | Temp. °C. | Benzene LHSV | Benzene Conv. % | Selectivity, Wt. % CH | $C_{12}H_{22}$ | MCPB | CHB | Heavies | Weight Ratio CHB/CH |
|---|---|---|---|---|---|---|---|---|---|---|
| 6  | 3 | 168 | 10   | 4.9  | 42.8      | 4.1  | 1.02 | 55.1 | —[a] | 1.3    |
| 7  | 3 | 175 | 10   | 5.8  | 34.5      | 0.86 | 1.72 | 62.1 | —    | 1.8    |
| 8  | 3 | 175 | 14   | 11.7 | 47.0      | 2.56 | 1.70 | 48.7 | —    | 1.0[b] |
| 9  | 4 | 200 | 9    | 10.6 | 96.2      | 0.94 | —    | 2.8  | —    | 0.03   |
| 10 | 5 | 155 | 10   | 0.1  | tr[c]     | —    | —    | 100  | —    | —      |
| 11 | 5 | 185 | 10   | 0.1  | tr        | —    | —    | 100  | —    | —      |
| 12 | 5 | 265 | 5.5  | 0.4  | 75.0      | —    | —    | 25.0 | —    | 0.33   |
| 13 | 6 | 200 | 11.6 | 14.1 | 97.2      | 0.71 | tr   | 2.1  | —    | 0.02   |

[a] A dash — indicates either not detected under the conditions of the analysis procedure or else no calculation made from GLC data.
[b] This run made after catalyst was regenerated by heating to about 500° C. in a flow of air at atmospheric pressure for about three hours.
[c] The symbol "tr" indicates a trace amount of material detected by the analysis.

The results shown in Table II indicate that these catalysts under the conditions employed are of very low activity and/or very low selectivity for cyclohexylbenzene production.

EXAMPLE III

Catalyst Preparation

Other catalysts were prepared for benzene hydroalkylation which were outside the scope of the instant invention. In one case (catalyst No. 7), the catalyst contained nickel, rare earths and platinum on a Type X crystalline zeolite which had been cation exchanged. However, in this case, the nickel was added to the cation-exchanged support along with the platinum in an impregnation step. This catalyst was prepared by utilizing the support material of catalyst No. 3 above as the support. The catalyst support for catalyst No. 3 was a cation exchanged Type X crystalline zeolite which had been exchanged with ammonium chloride and rare earth chlorides and then calcined under the conditions indicated. A portion (20 grams) of this crystalline zeolite material which had been cation exchanged and then calcined was impregnated with a solution of 0.0531 grams of chloroplatinic acid hexahydrate and 4.66 grams of nickel nitrate [Ni(No$_3$)$_2$] hexahydrate in about 80 ml of absolute ethanol under total impregnation conditions. The ethanol solvent was then removed under vacuum on a rotary evaporator. The catalyst (No. 7) thus contained 0.1% platinum, 4.7% nickel, 16.37% rare earths and 0.65% sodium by weight.

Another catalyst was prepared which contained nickel, rare earths and platinum on an acidic crystalline zeolite of Type X but which also contained a small amount of ruthenium as an added catalyst component. This catalyst (No. 8) was prepared by cation exchanging 250 grams of a Type X crystalline zeolite (Davison 13X molecular sieves) with a solution of 400 grams of ammonium chloride, 100 grams of rare earth chlorides and 400 grams of nickel chloride hexahydrate in 4 liters of water in a manner essentially the same as that described above. The cation exchanged zeolite was filtered and washed and allowed to dry in the air as described above. About one-half of the cation-exchanged zeolite was calcined under conditions essentially the same as those described above to provide a support material which contained 6.5% nickel and 0.72% sodium. A portion (41.2 grams) of the uncalcined cation-exchanged material was impregnated with a solution of 0.08 grams of chloroplatinic acid hexahydrate and 0.081 grams of ruthenium trichloride in 50 ml of distilled water. The water was evaporated to dryness on a rotary evaporator. The impregnated support was then calcined by heating to about 204° C. (400° F.) overnight and then increasing the temperature to about 518° C. (965° F.) over an 8 hour period. The calcined catalyst was allowed to cool in ambient air and was then ready for utilization in benzene hydroalkylation runs. The final catalyst thus contained 0.1% platinum, 0.1% ruthenium, 6.5% nickel and 0.72% sodium by weight. In this instance, the analysis for the rare earths was not carried out but based on previous experience the rare earth metal content was estimated to be 9–10% by weight.

In another catalyst preparation (No. 9) another element was also added to the catalyst of nickel, rare earths, and platinum on an acidic Type X molecular sieve. In this instance, tin was the added element and the preparation was carried out as follows. The cation exchange conditions for the crystalline zeolite were the same as those used for the preparation of the support for catalyst No. 1 of Example I above. A portion (41 grams) of the support material was impregnated with a solution of 0.16 grams of chloroplatinic acid hexahydrate and 0.07 grams of stannous chloride (SnCl$_2$) dihydrate in 50 ml of distilled water. The water was evaporated at reduced pressure and the resultant material calcined under conditions similar to those utilized in the preparations above, namely, heating of the impregnated crystalline zeolite to about 200° C. (392° F.) overnight followed by raising the temperature to about 516° C. (960° F.) over an 8 hour period. The material was allowed to cool in air and was ready for utilization in benzene hydroalkylation runs. Based on previous experience and analyses for the support of catalyst No. 1, the catalyst thus prepared was believed to have contained 0.2% platinum, 4.68% nickel, 9.5% rare earths and 0.63% sodium by weight. The amount of tin charged to the catalyst in the impregnation step was on an equimolar basis with the amount of platinum also added in the impregnation step.

Benzene Hydroalkylation

The catalysts prepared as described above were utilized in benzene hydroalkylation runs at a hydrogen pressure of 3,450 kPa (500 psig) and a hydrogen flow rate of 0.32 liters per minute. The other reaction conditions employed as well as the results obtained in these runs are shown below in Table III.

Table III

| Run No. | Catalyst No. | Temp. °C. | Benzene LHSV | Benzene Conv. % | CH | Selectivity, Wt. % $C_{12}H_{22}$ | MCPB | CHB | Heavies | Weight Ratio CHB/CH |
|---|---|---|---|---|---|---|---|---|---|---|
| 14 | 7 | 150 | 12 | 3.6 | 97.2 | — | — | 2.8 | — | 0.03 |
| 15 | 7 | 200 | 12 | 10.8 | 94.4 | 1.85 | — | 3.7 | — | 0.04 |
| 16 | 8 | 160 | 18 | 6.4 | 54.7 | 1.25 | 1.88 | 42.2 | — | 0.8 |
| 17 | 9 | 155 | 13 | 8.1 | 14.8 | 0.62 | 1.11 | 76.5 | 7.4 | 5.2 |
| 18 | 9 | 175 | 11.5 | 5.8 | 17.2 | 0.86 | 1.55 | 82.7 | — | 4.8 |

These runs indicate that under the reaction conditions employed the impregnation of the support material with nickel and platinum was not as effective in producing an active catalyst as by exchange of the support with nickel followed by impregnation with platinum. Furthermore, the addition of ruthenium to the catalyst seemed to harm catalyst selectivity while the addition of the tin compound appeared to have little, if any, effect, on activity or selectivity of the catalyst under the process conditions employed.

EXAMPLE IV

Catalyst Preparation

A number of other catalysts were prepared according to the instant invention in which the amounts of nickel or platinum were varied in the preparation of the catalysts. All of the catalysts were prepared utilizing a Type X crystalline zeolite (Davison 13X mole sieves). In each instance, the crystalline zeolite was cation exchanged with a solution of ammonium chloride (10% by weight), rare earth chlorides (2.5% by weight) and nickel chloride in the manner described in Example I for catalyst No. 1. After the cation exchange step, the catalysts were impregnated with chloroplatinic acid in the manner previously described for catalyst No. 1 and then calcined following the impregnation step to provide catalysts suitable for use in benzene hydroalkylation runs. Concentration of the cation exchange solution in terms of the nickel chloride for the preparation of these catalysts and the analytical results for the catalysts in terms of platinum, nickel, rare earth and sodium content is presented below in Table IV.

Table IV

| Catalyst No. | Wt. % $NiCl_2$ in Cation Exchange Sol'n | Final Catalyst, Wt. % Pt | Ni | RE | Na |
|---|---|---|---|---|---|
| 10 | 2.5 | 0.1 | 3.18 | 10–11[a] | 0.68 |
| 11 | 10 | 0.1 | 6.5 | 9–10[a] | 0.72 |
| 12 | 10 | 0.2 | 6.5 | 9–10[a] | 0.72 |
| 13 | 5 | 0.15 | 4.68 | 9.5 | 0.63 |
| 14 | 5 | 0.15 | 4.68 (+0.15)[b] | 9.5 | 0.63 |
| 15 | 2.5 | 0.10 | 3.18 | 10–11[a] | 0.68 |
| 16 | 2.5 | 0.15 | 3.18 | 10–11[a] | 0.68 |
| 17 | 2.5 | 0.15 | 3.18 (+0.15)[b] | 10–11[a] | 0.68 |

[a] No actual analysis made; RE value was estimated based on previous experience with such compositions.
[b] Additional nickel chloride added in the impregnation step.

Benzene Hydroalkylation

The catalysts prepared according to the instant invention as described above were employed in benzene hydroalkylation runs in the continuous reaction system previously described. The hydrogen pressure in each of the runs was maintained at 3,450 kPa (500 psig) at a flow rate of 0.32 liters per minute. Other conditions utilized in these runs as well as the results obtained are presented below in Table V.

TABLE V

| Run No. | Catalyst No. | Temp. °C. | Benzene LHSV | Benzene Conv. % | CH | Selectivity, Wt. % $C_{12}H_{22}$ | MCPB | CHB | Heavies | Weight Ratio CHB/CH |
|---|---|---|---|---|---|---|---|---|---|---|
| 19 | 10 | 170 | 18.7 | 11.7 | 23.1 | 0.85 | 1.71 | 74.4 | — | 3.5 |
| 20 | 11 | 160 | 20 | 7.8 | 19.2 | 0.77 | 1.54 | 69.2 | 9.2 | 3.6 |
| 21 | 12 | 160 | 16.7 | 7.3 | 50.7 | 4.11 | 1.37 | 43.8 | — | 0.9 |
| 22 | 12 | 164 | 16 | 9.6 | 20.8 | 0.73 | 1.04 | 60.4 | 9.4 | 2.9 |
| 23 | 13 | 170 | 14.7 | 9.1 | 16.5 | 0.66 | 1.54 | 70.8 | 10.4 | 4.3 |
| 24 | 13 | 180 | 20 | 9.6 | 14.0 | 0.83 | 1.56 | 74 | 9.4 | 5.3 |
| 25 | 13 | 195 | 20 | 6.5 | 23.1 | 0.12 | 0.25 | 73.8 | — | 3.2 |
| 26 | 13 | 180 | 17.8 | 4.7 | 29.8 | 0.42 | 1.70 | 68.1 | — | 2.3 |
| 27 | 14 | 160 | 17 | 11.2 | 15.2 | 0.89 | 1.78 | 73.2 | 8.9 | 4.8 |
| 28 | 14 | 173 | 20 | 11.1 | 15.3 | 0.90 | 1.80 | 73 | 9 | 4.8 |
| 29 | 15 | 170 | 6.7 | 7.1 | 21.1 | 1.41 | 1.41 | 64.8 | 11.3 | 3.1 |
| 30[a] | 15 | 172 | 13.3 | 5.2 | 23.1 | 0.38 | 1.35 | 67.3 | 6.5 | 2.9 |
| 31 | 16 | 170 | 13.3 | 9.3 | 47.3 | 0.54 | 0.54 | 51.6 | — | 1.1 |
| 32 | 16 | 195 | 13.3 | 12.9 | 37.2 | 0.78 | 2.32 | 59.7 | — | 1.6 |
| 33 | 17 | 172 | 10 | 7.4 | 40.5 | 1.35 | 1.35 | 56.8 | — | 1.4 |
| 34 | 17 | 185 | 9.2 | 9.2 | 29.3 | 2.17 | 2.17 | 66.3 | — | 2.2 |

[a] Run made after regeneration of catalyst by heating in flowing air to about 500° C. for about 2 hours.

Of the above runs, Run 24 employing catalyst 13 and Runs 27 and 28 employing catalyst No. 14 appeared to produce the best overall results under the conditions employed considering both conversion of benzene and selectivity to cyclohexylbenzene.

EXAMPLE V

Catalyst Preparation

Other catalysts were prepared which were outside the scope of the instant invention. In the preparation of these catalysts, an attempt was made to substitute magnesium chloride for all of the nickel chloride, to substitute magnesium chloride for a portion of the nickel chloride, and to substitute iron chloride ($FeCl_3$) for nickel chloride in the catalyst preparation.

Catalyst No. 18 was prepared by first carrying out a cation exchange of a crystalline zeolite of Type X (Davison 13X mole sieves). A solution of 400 grams of ammonium chloride, 100 grams of rare earth chlorides and 100 grams of magnesium chloride ($MgCl_2$) hexahydrate in 4 liters of water was prepared. A portion of the above solution was utilized to wet 200 grams of the crystalline zeolite and the zeolite then charged to the cation exchange reactor previously utilized. The cation exchange reaction was carried out under the conditions described above, i.e. 0.25 LHSV at about 100° C. The cation-exchanged crystalline zeolite was cooled, filtered, and washed six times with 350 ml portions of water and then allowed to dry over the weekend. A portion (20 grams) of the above described cation-exchanged crystalline zeolite, which also had been calcined under the usual calcination conditions for the catalysts of this invention, was impregnated with 0.0519 grams of chloroplatinic acid hexahydrate in about 60 ml of absolute ethanol. The ethanol was removed on a rotary evaporator and the catalyst was then ready for use in benzene hydroalkylation runs. The catalyst thus contained 0.1% platinum, 9.35% magnesium, and 0.75% sodium. No analysis for rare earth metal content was carried out for this catalyst but based on previous experience the estimated value was 5-6% by weight.

Catalyst No. 19 was prepared by utilizing the same cation-exchanged crystalline zeolite in the preparation of Catalyst No. 18. In this instance, however, the impregnation of a portion (20 grams) of the cation exchanged zeolite was carried out with a solution of 0.0536 grams of chloroplatinic acid hexahydrate and 0.0810 grams of nickel chloride hexahydrate in about 80 ml of absolute ethanol. The ethanol was removed on a rotary evaporator to provide the catalyst ready for use in benzene hydroalkylation runs. This catalyst (No. 19) contained 0.1% platinum, 0.1% nickel, 9.35% magnesium, 0.75% sodium. The rare earth metal content was not determined but based on previous experience was estimated to be 5-6% by weight.

Catalyst No. 20 was prepared by carrying out a cation exchange reaction with 200 grams of the Type X crystalline zeolite (Davison 13X molecular sieves) with a solution of 400 grams of ammonium chloride, 100 grams of the rare earth chlorides and 100 grams of ferric chloride ($FeCl_3$) hexahydrate in 4 liters of distilled water. The cation exchange process was carried out under essentially the same conditions utilized for the preparation of catalyst No. 18 above. Some difficulty was encountered in filtering and washing the cation exchange material but this was accomplished and the material allowed to dry over a three day period. The cation-exchanged crystalline zeolite was calcined under the usual conditions for the catalysts of this invention and a portion (20 grams) of the calcined material was impregnated with 0.0536 grams of chloroplatinic acid hexahydrate in about 80 ml of absolute ethanol. The ethanol was removed on a rotary evaporator to provide a catalyst ready for use in benzene hydroalkylation runs. The catalyst contained 0.1% platinum by weight but no analysis was carried out for the rare earth, sodium or iron in the catalytic material but based on previous experience the estimated values were about 3% by weight iron, about 0.7% by weight sodium and 10-11% by weight rare earth metals.

Benzene Hydroalkylation

Each of the catalysts described above were employed in the hydroalkylation of benzene in the continuous reaction system previously described. Hydrogen pressure was maintained at 3,450 kPa (500 psig) and at a flow rate of 0.32 liters per minute. Other conditions employed in the hydroalkylation runs and the results obtained in the runs are presented below in Table VI.

TABLE VI

| Run No. | Catalyst No. | Temp. °C. | Benzene LHSV | Benzene Conv. % | Selectivity, wt. % CH | $C_{12}H_{22}$ | MCPB | CHB | Heavies | Weight Ratio CHB/CH |
|---|---|---|---|---|---|---|---|---|---|---|
| 35 | 18 | 165 | 6.7 | 6.8 | 55.9 | 0.74 | 0.74 | 42.6 | — | 0.8 |
| 36 | 19 | 166 | 11 | 1.5 | 53.3 | — | — | 46.7 | — | 0.9 |
| 37 | 20 | 174 | 18.5 | 6.4 | 51.5 | 0.78 | 0.78 | 46.9 | — | 0.9 |

The catalyst used in Runs 35 and 37 provided relatively poor benzene conversion and very poor selectivity to cyclohexylbenzene under the conditions employed. The catalyst used in Run 36 was very poor in both categories of performance under the conditions employed.

EXAMPLE VI

Catalyst Preparation

Other catalysts were prepared which were outside the scope of the instant invention. Catalyst No. 21 was prepared in the manner similar to that utilized for the preparation of Catalyst No. 7 shown in Example III above. In this instance, however, the crystalline zeolite support material was different from that utilized in the preparation of catalyst No. 7, i.e. a Linde 10X molecular sieve of 10-14 mesh was used for No. 21. Two hundred grams of the Linde 10X mole sieve was wetted with a portion of a solution of 400 grams of ammonium chloride and 200 grams of rare earth chlorides in 4 liters of water. The wetted mole sieve material was charged to the cation exchange reactor previously employed and the remainder of the solution of ammonium chloride and rare earth chlorides was pumped over the zeolite material at about 95° C. and at about 0.25 LHSV. The cation-exchanged material was cooled, filtered and washed six times with 350 ml portions of water and then allowed to dry in ambient air. The cation-exchanged material was then calcined under the usual conditions employed for the catalysts of this invention. A portion (30 grams) of the calcined zeolite material was impregnated with a solution of 0.0823 grams of chloroplatinic acid hexahydrate and 0.1218 grams of nickel chloride hexahydrate in about 80 ml of absolute ethanol. The ethanol was removed under reduced pressure on a rotary evaporator and the catalyst was then ready for use in benzene hydroalkylation runs. The catalyst thus prepared contained 0.1% platinum, 0.1% nickel and 0.38% sodium. Analysis for rare earth metal content was not carried out on this catalyst but based on previous experience the value was estimated to be 15-16% by weight.

Catalyst No. 22 was prepared utilizing a Type Y crystalline zeolite as the support material but the catalyst was prepared such that no rare earths were present in the final catalyst composite. Two hundred and fifty grams of a Type Y crystalline zeolite (SK-40 of 10-14 mesh from Linde Division of Union Carbide Corporation) was wetted with a portion of a solution of 400 grams of ammonium chloride, 200 grams of nickel chloride hexahydrate in 4 liters of distilled water and then charged to the cation exchange reactor previously employed. The cation exchange process was carried out at about 100° C. and at about 0.25 LHSV. The cation-exchanged material was cooled, filtered and washed six times with 350 ml portions of water and then allowed to dry in ambient air overnight. The cation-exchanged zeolite was then calcined under the usual conditions employed and previously described for catalysts of the instant invention. A portion (39.47 grams) of this cation-exchanged and calcined material was impregnated with 0.0798 grams of chloroplatinic acid hexahydrate in about 80 ml of absolute ethanol. The ethanol was removed under reduced pressure on a rotary evaporator. The catalyst thus prepared contained 0.1% platinum, 1.80% nickel and 1.40% sodium.

Two other catalysts outside the scope of the instant invention were prepared utilizing a Type A crystalline zeolite material whose pore diameters were about five angstroms. Catalyst No. 23 was prepared by wetting 200 grams of a crystalline zeolite material commercially available of about five angstroms pore diameter (Davison 5A mole sieves of 8-12 mesh) with a portion of a solution of 400 grams of ammonium chloride, 100 grams of rare earth chlorides and 100 grams of nickel chloride hexahydrate in 4 liters of distilled water. The remainder of the solution was pumped over the zeolite in the cation exchange reactor previously employed while the cation exchange process took place at about 100° C. and at about 0.25 LHSV. The cation-exchanged zeolite was cooled, filtered and washed six times with 350 ml portions of water and allowed to dry in ambient air. A portion (41.7 grams) of the cation-exchanged zeolite of five angstrom pore diameter was impregnated with 0.0795 grams of chloroplatinic acid hexahydrate in about 50 ml of absolute ethanol and the ethanol removed on a rotary evaporator under reduced pressure. The material was then calcined under the usual conditions employed for the catalysts of this invention. The catalyst contained 0.1% platinum, 4.6% nickel, and 0.31% sodium. Rare earth content of the catalyst was not determined.

Catalyst No. 24 different from catalyst No. 23 only in the impregnation step which was carried out as follows. A portion (41.7 grams) of the cation exchanged crystalline zeolite of five angstrom pore diameter prepared as described above for catalyst No. 23 was impregnated with a solution of 0.0791 grams of chloroplatinic acid hexahydrate and 0.1204 grams of nickel chloride hexahydrate in about 80 ml of absolute ethanol. The ethanol was removed under reduced pressure in a rotary evaporator and the material calcined in the same furnace with catalyst No. 23. This catalyst (No. 24) contained 0.1% platinum, 4.6% nickel plus an additional 0.1% nickel by impregnation and 0.31% sodium. Rare earth content for this catalyst was not determined.

Catalyst No. 25 was prepared utilizing a Type X crystalline zeolite (Davison 13X mole sieves) but with cobalt instead of nickel in the catalyst for the hydroalkylation reaction. The catalyst was prepared by wetting 250 grams of the crystalline zeolite with a portion of a solution of 400 grams of ammonium chloride, 100 grams of rare earth chlorides and 200 grams of cobalt chloride ($CoCl_2$) hexahydrate in 4 liters of distilled water. The wetted crystalline zeolite was charged to the cation exchange reactor previously employed and the cation exchange process carried out at about 100° C. and at about 0.25 LHSV. The remainder of the above described solution was pumped over the crystalline zeolite bed in the cation exchange reactor under the conditions indicated. The material was cooled, filtered and washed six times with 350 ml portions of water and allowed to dry in the air. A portion (30 grams) of the cation-exchanged crystalline zeolite was impregnated with a solution of 0.0549 grams of chloroplatinic acid hexahydrate in about 80 ml of absolute ethanol. The ethanol was removed under reduced pressure on a rotary evaporator and the recovered material then calcined under essentially the same conditions previously employed for the catalysts of this invention. The catalyst thus obtained contained 0.1% platinum but no analysis was carried out for rare earth, cobalt or sodium content of the catalyst but based on previous experience the estimated values were 4-5% by weight cobalt, 9-10% by weight rare earth metals and about 0.6% by weight sodium.

Catalyst Nos. 21, 22, 23, 24 and 25 were utilized in benzene hydroalkylation runs described below.

Benzene Hydroalkylation

The catalysts described above were utilized for benzene hydroalkylation under 3,450 kPa (500 psig) of hydrogen at a flow rate of 0.32 liters per minute of hydrogen. Other conditions utilized in the hydroalkylation runs carried out in the continuous reaction system previously employed are shown in Table VII along with the results obtained in the hydroalkylation runs.

TABLE VII

| Run No. | Catalyst No. | Temp. °C. | Benzene | | Selectivity, Wt. % | | | | | Weight Ratio CHB/CH |
|---|---|---|---|---|---|---|---|---|---|---|
| | | | LHSV | Conv. % | CH | $C_{12}H_{22}$ | MCPB | CHB | Heavies | |
| 38 | 21 | 170 | 7.3 | 7.0 | 28.6 | 0.70 | 0.70 | 70.0 | — | 2.4 |
| 39 | 22 | 230 | 17.8 | 7.8 | 75.6 | 0.06 | 0.19 | 2.2 | — | 0.3 |
| 40 | 23 | 180 | 20 | 11.3 | 98.2 | — | — | 1.2 | — | 0.02 |
| 41 | 23 | 200 | 20 | 8.7 | 97.7 | — | — | 2.3 | — | 0.02 |
| 42 | 24 | 185 | 20 | 6.4 | 100 | — | — | — | — | — |
| 43 | 24 | 215 | 15 | 7.4 | 97.3 | 1.35 | — | 0.35 | — | — |

TABLE VII-continued

| Run No. | Catalyst No. | Temp. °C. | Benzene LHSV | Benzene Conv. % | CH | $C_{12}H_{22}$ | MCPB | CHB | Heavies | Weight Ratio CHB/CH |
|---|---|---|---|---|---|---|---|---|---|---|
| 44 | 25 | 175 | 10 | 8.1 | 42.4 | 2.47 | 1.23 | 51.5 | — | 1.2 |

With the exception of catalyst No. 21, the catalysts of this Example demonstrated rather low selectivity to the desired product, cyclohexylbenzene. It can also be seen that catalyst No. 21 gave much better results than similarly prepared catalyst No. 7.

EXAMPLE VII

Catalyst Preparation

A large quantity of hydroalkylation catalyst made according to the instant invention was prepared in a manner essentially the same as that utilized in the preparation of catalyst No. 1 in Example I. In the present case, catalyst No. 26 was prepared by utilizing solutions of 400 grams of ammonium chloride, 100 grams of rare earth chlorides and 200 grams of nickel chloride hexahydrate in 4 liters of distilled water. A portion of this solution was utilized to wet 431 grams of a Type X crystalline zeolite (Davison 13X mole sieves) and the wetted zeolite charged to the cation exchange reactor utilized previously. Additional solution was pumped over the zeolite bed at about 100° C. and at about 0.25 LHSV. The zeolite was then cooled, filtered and washed six times with 500 ml portions of water and then allowed to dry overnight in ambient air to give 520.8 grams of material. The above procedure was repeated utilizing 326.3 grams of the same Type X crystalline zeolite and the same solution for cation exchange described above. The cation exchange conditions were essentially the same for this second batch of catalyst support and the recovered crystalline zeolite was cooled, filtered and washed as before. This material weighed 420.3 grams after drying in ambient air.

A solution of 0.75 grams of chloroplatinic acid hexahydrate and 300 ml of water was utilized to impregnate 400 grams of the above described cation-exchanged crystalline zeolite. The water was removed under reduced pressure in a rotary evaporator and the recovered material calcined under the usual conditions employed for the catalysts of this invention. The recovered product from calcination weighed 281.6 grams. The impregnation and calcination of another 400 gram batch of the cation-exchanged crystalline zeolite was carried out under essentially the same conditions to give 281.7 grams for a total of 563.3 grams of the catalyst which contained 0.1% platinum.

Catalyst No. 27 was prepared by utilizing the cation-exchanged crystalline zeolite obtained during the preparation of catalyst No. 26 described above as the support material for an impregnation of 50 grams of the cation exchange support with a solution of 0.093 grams of chloroplatinic acid hexahydrate and 1.75 grams of 12-tungstosilicic acid in 50 ml of water. The water was removed under reduced pressure and the product then calcined under the usual conditions.

Benzene Hydroalkylation

The catalysts (Nos. 26 and 27) prepared as described above were utilized in benzene hydroalkylation runs under 3,450 kPa (500 psig) hydrogen pressure at a flow rate of 0.32 liters per minute of hydrogen. Other reaction conditions and the results obtained in the hydroalkylation runs are presented below in Table VIII. The hydroalkylation runs were carried out in the continuous operation system previously employed unless otherwise indicated in the table. Regeneration, when utilized, involved heating the catalyst in flowing air at 400°–450° C. for 2–4 hours.

TABLE VIII

| Run No. | Catalyst No. | Temp. °C. | Benzene LHSV | Benzene Conv. % | CH | $C_{12}H_{22}$ | MCPB | CHB | Heavies | Weight Ratio CHB/CH |
|---|---|---|---|---|---|---|---|---|---|---|
| 45 | 26 | 173 | 10 | 12.1 | 16.7 | 0.66 | 1.40 | 72.7 | 8.3 | 4.4 |
| 46[a] | 26 | 163–171 | 11.6 | 8.0 | 14.8 | — | — | 73.8 | 7.2 | 5.0[d] |
| 47[b] | 26 | 174 | 10 | 1.0 | 30 | — | — | 70 | — | 2.2 |
| 48[c] | 26 | 169 | 20 | 9.1 | 9.3 | 1.09 | 2.20 | 76.4 | 11.0 | 8.2 |
| 49[c] | 26 | 182 | 20 | 9.5 | 15.0 | 0.53 | 3.15 | 81.7 | — | 5.4 |
| 50[c] | 26 | 162 | 20 | 9.0 | 14.7 | 1.17 | 1.50 | 73.5 | 9.1 | 5.0 |
| 51[c] | 26 | 160 | 20 | 10.0 | 14.0 | 0.70 | 0.60 | 74.2 | 10.0 | 5.3 |
| 52[c] | 26 | 162 | 20 | 7.0 | 14.4 | 0.98 | 0.44 | 71.8 | 12.5 | 5.0 |
| 53[b] | 26 | 178 | 20 | 2.1 | 11.4 | — | — | 77.9 | — | 6.8 |
| 54[c] | 26 | 156 | 20 | 8.9 | 13.3 | — | — | 76.6 | — | 5.8 |
| 55[c] | 26 | 180 | 20 | 6.6 | 12.6 | — | — | 77 | — | 6.1 |
| 56 | 27 | 173 | 14 | 8.2 | 23.3 | 0.66 | 1.54 | 65.4 | 9.1 | 2.8 |
| 57 | 27 | 169 | 10 | 8.2 | 19.6 | tr | 1.66 | 71.2 | 9.1 | 3.6 |

[a]This run made in a scaled-up pilot plant continuous operation system.
[b]This was made with a catalyst which had been used previously in pilot plant runs and not regenerated.
[c]These runs made with regenerated catalyst from pilot plant runs.
[d]Analysis for this run made by distillation of accumulated effluent.

Of the above runs, Runs 48 and 54 provided the best results under the conditions employed; however, operability of both catalysts 26 and 27 were demonstrated.

EXAMPLE VIII

Catalyst Preparation

Two other catalysts were prepared according to the procedures of the instant invention. In each case, the mixture of rare earth chlorides previously employed in the catalyst preparations was replaced by single rare earth compound. In catalyst No. 28 200 grams of a Type X crystalline zeolite (Davison 13X mole sieves) was wetted with a portion of a solution of 400 grams of ammonium chloride, 200 grams of nickel chloride hexahydrate and 100 grams of lanthanum chloride ($LaCl_3$)

hexahydrate in 4 liters of deionized water. The crystalline zeolite material was then charged to the cation exchange reactor previously employed and the remainder of the above described solution pumped over the zeolite bed at a temperature of about 98° C. and at about 0.25 LHSV. The material was cooled, filtered and washed six times with 350 ml portions of water and then permitted to dry in ambient air. A portion (50 grams) of the cation-exchanged crystalline zeolite was impregnated with a solution of 0.0905 grams of chloroplatinic acid hexahydrate in about 50 ml of absolute ethanol. The ethanol was removed under reduced pressure, more ethanol added and then removed as before. The recovered material was heated under calcination conditions similar to those previously employed, that is, heating up to about 205° C. (401° F.) and holding at this temperature overnight followed by heating over an 8 hour period up to about 524° C. (975° F.). This catalyst contained 0.1% platinum but no analysis was performed for nickel, lanthanum and sodium content. However, based on previous experience the estimated values were 4–5% by weight nickel, 9–10% by weight lanthanum and about 0.6% by weight sodium.

Catalyst No. 29 was prepared in essentially the same manner as catalyst No. 28 with the exception that cerous chloride (CeCl$_3$) was utilized in the place of lanthanum chloride in the cation exchange step. The cation-exchanged material was impregnated with a solution of 0.0966 grams of chloroplatinic acid hexahydrate in about 50 ml of absolute ethanol. The ethanol was removed under reduced pressure and additional ethanol added and then removed as before. The catalyst was calcined under essentially the same conditions utilized for catalyst No. 28. This catalyst also contained 0.1 wt. % platinum but no analysis was made for nickel, cerium and sodium. However, based on previous experience the estimated values were 4–5% by weight nickel, 9–10% by weight cerium, and about 0.6% by weight sodium.

Benzene Hydroalkylation

The catalysts described above (Nos. 28 and 29 were employed in benzene hydroalkylation runs utilizing a hydrogen pressure of 3,450 kPa (500 psig) and a hydrogen flow rate of 0.32 liters per minute. Other reaction conditions employed as well as the results of the hydroalkylation runs are presented in Table IX below.

stance, 30 grams of a 10–14 mesh commercially available silica-alumina cracking catalyst (Durabead 8) was impregnated with a solution of 0.0805 grams of chloroplatinic acid hexahydrate and 0.1214 grams of nickel chloride hexahydrate in about 80 ml of absolute ethanol. The ethanol was removed under reduced pressure on a rotary evaporator. This catalyst (No. 30) contained 0.1% platinum and 0.1% nickel but no analysis was performed for sodium content. Based on available composition analysis provided by the supplier, the estimated sodium content was 1–2% by weight.

Benzene Hydroalkylation

Catalyst No. 30 prepared as described above was employed in a benzene hydroalkylation run, Run No. 62, under the following conditions: 3,450 kPa (500 psig) hydrogen, 0.32 liters per minute hydrogen flow, 210° C., 6.7 LHSV benzene feed, and in the continuous reaction system previously employed. The results showed a benzene conversion of 11.0% and a weight percent selectivity as determined by gas-liquid chromatography analysis of 54.5% to cyclohexane (CH), 0.90% to $C_{12}H_{22}$, 0.9% to MCPB and 43.6% to cyclohexylbenzene (CHB). This analysis indicated a weight ratio of CHB/CH of 0.8. The results thus indicate that catalyst No. 30 had very low selectivity to the production of cyclohexylbenzene when compared with the catalysts of the instant invention.

EXAMPLE X

The productivity and activity duration were studied for catalyst No. 1 prepared as described in Example 1 above. In this run, Run 63, a 5.5 gram charge of catalyst No. 1 was placed in a reaction zone equipped with heating means and for continuous operation.

This long term study demonstrated that the above catalyst charge could be maintained at high productivity for more than 123 days (2,950 hours) of continuous hydroalkylation of benzene yielding more than 8,000 grams of cyclohexylbenzene during the run. The extended run was carried out for more than eight cycles, each cycle consisting of a run period of 11–25 days (3,450 kPa hydrogen pressure, 150° C. increasing gradually to 180° C.) with a 7 hour catalyst regeneration in air to a final regeneration temperature of about 400°–515° C. Benzene feed rate was at about 10 LHSV and conversion was maintained at about 5% by the indicated Table IX

| Run No. | Catalyst No. | Temp. °C. | Benzene LHSV | Benzene Conv. % | Selectivity, Wt. % CH | $C_{12}H_{22}$ | MCPB | CHB | Heavies | Weight Ratio CHB/CH |
|---|---|---|---|---|---|---|---|---|---|---|
| 58 | 28 | 153 | 20 | 7.5 | 31.7 | — | — | 67.2 | — | 2.1 |
| 59[a] | 28 | 185 | 23 | 13.6 | 23.2 | 0.37 | 1.84 | 75.0 | — | 3.2 |
| 60 | 28 | 210 | 20 | 14.5 | 32.4 | 0.34 | 1.03 | 63.4 | — | 1.9 |
| 61 | 29 | 203 | 20 | 12.2 | 51.6 | 1.23 | 1.23 | 45.9 | — | 0.9 |

[a]Run made after regeneration of the catalyst by heating to about 450° C. for about 4 hours in flowing air.

The above results indicate that use of single rare earth compounds rather than the previously employed mixture of rare earth compounds produces hydroalkylation catalysts of reduced effectiveness. This appears to be especially true when cerium alone is utilized as the rare earth component.

EXAMPLE IX

Catalyst Preparation

Another catalyst, No. 30, was prepared which is outside the scope of the instant invention. In this instance, gradual increase in temperature from 150° to 180° C. during the onstream period. Selectivity to cyclohexylbenzene during this extended run was about 80 to 85%. It was also noted during this run that a water content of about 20–50 ppm in the benzene seem to promote highest selectivity to cyclohexylbenzene and a minimizing of by-product formation.

Continuation of the above described run indicated that catalyst No. 1 lifetime for benzene hydroalkylation is exceedingly long and that regeneration appears to be readily accomplished by well known techniques. These results indicate the commercial utility of a catalyst prepared according to the instant invention.

What is claimed is:

1. A composition comprising:
   at least one platinum compound supported on a calcined, acidic, nickel and rare earth-treated crystalline zeolite wherein the rare earth content of the calcined, acidic, nickel and rare earth-treated crystalline zeolite is within a range of from about 2 to about 25 percent by weight of the composition.

2. The composition of claim 1 wherein the platinum content ranges from about 0.01 to about 1 percent by weight.

3. The composition of claim 1 wherein the platinum content ranges from about 0.05 to about 0.25 percent by weight.

4. The composition of claim 1 wherein the crystalline zeolite is selected from the group consisting of Type X and Type Y zeolites;
   wherein the rare earth metal and nickel compounds are selected from the group consisting of nitrates, bromides, acetates, chlorides, iodides, sulfates and mixtures thereof;
   wherein the rare earth metal is selected from the group consisting of cerium, lanthanum, praseodymium, neodymium, samarium, europium, gadolinium, terbium, dysprosium, holmium, erbium, thulium, ytterbium, lutetium and mixtures thereof, and
   wherein the platinum compound is selected from the group consisting of ammonium hexachloroplatinate (IV), ammonium tetrachloroplatinate (II), chloroplatinic acid, diaminoplatinum dinitrite, platinic acid, platinum tetrachloride and mixtures thereof.

5. The composition of claim 1 wherein the crystalline zeolite is the alkali metal form with the alkali metal content of the calcined, acidic, nickel and rare earth-treated crystalline zeolite in the range of from about 0.01 to about 2 percent by weight;
   wherein the nickel content of the calcined, acidic, nickel and rare earth-treated crystalline zeolite ranges from about 0.01 to about 15 percent by weight.

6. The composition of claim 1 wherein the crystalline zeolite is the alkali metal form with the alkali metal content of the calcined, acidic, nickel and rare earth-treated crystalline zeolite ranges from about 0.05 to about 1 percent by weight;
   wherein the rare earth content of the calcined, acidic, nickel and rare earth-treated crystalline zeolite ranges from about 5 to about 20 percent by weight; and
   wherein the nickel content of the calcined, acidic, nickel and rare earth-treated crystalline zeolite ranges from about 1 to about 8 percent by weight.

7. The composition of claim 1 wherein the crystalline zeolite is selected from the group consisting of Type X and Type Y zeolites; and
   the platinum compound is chloroplatinic acid, the nickel compound used to treat the crystalline zeolite is nickel chloride hexahydrate and the rare earth metal compound used to treat the crystalline zeolite is a mixture of the chlorides consisting of lanthanum, cerium, praseodymium, neodymium, samarium and gadolinium.

8. A method for the preparation of a composition comprising:
   contacting a crystalline zeolite with an aqueous cation exchange solution comprising rare earth, nickel, and ammonium compounds;
   removing the cation exchanged zeolite from said solution and washing said zeolite with water to remove excess ions;
   calcining said cation exchanged zeolite;
   cooling said calcined zeolite;
   impregnating said cation exchanged zeolite with a solution comprising at least one platinum compound in a suitable solvent; and
   removing said solvent by evaporation,
   wherein said cation exchanged zeolite is calcined and then cooled either before or after said platinum compound is impregnated on said zeolite wherein the rare earth content of the calcined, acidic, nickel and rare earth-treated crystalline zeolite is within a range of from about 2 to about 25 percent by weight of the composition.

9. The method of claim 8 wherein said zeolite is selected from the group consisting of alkali metal Type X and Type Y zeolites;
   wherein the rare earth metal and nickel compounds are selected from the group consisting of nitrates, bromides, acetates, chlorides, iodides, sulfates and mixtures thereof;
   wherein the rare earth metal is selected from the group consisting of cerium, lanthanum, praseodymium, neodymium, samarium, europium, gadolinium, terbium, dysprosium, holmium, erbium, thulium, ytterbium, lutetium and mixtures thereof, and
   wherein the platinum compound is selected from the group consisting of ammonium hexachloroplatinate (IV), ammonium tetrachloroplatinate (II), chloroplatinic acid, diaminoplatinum dinitrite, platinic acid, platinum tetrachloride and mixtures thereof;
   wherein the weight ratio of ammonium compound to rare earth and nickel compounds ranges from about 0.05:1 to about 20:1;
   wherein said aqueous cation exchange nickel, rare earth and ammonium compound solution is contacted with said zeolite at a liquid hourly space velocity ranging from about 0.1 to about 0.5; and
   wherein after said zeolite is washed with water and prior to said calcination step, said zeolite is heated to a temperature ranging from about 100° to 300° C. to remove excess water and then the temperature is slowly raised to a temperature ranging from about 200° to 550° C. in order to calcine said zeolite and convert the ammonium cations to the hydrogen form.

10. The method of claim 9 wherein said composition is treated with hydrogen subsequent to the removal by evaporation of the platinum compound solvent.

11. The method of claim 8 wherein the crystalline zeolite is selected from the group consisting of Type X and Type Y zeolites; and
    the platinum compound is chloroplatinic acid, the nickel compound used to treat the crystalline zeolite is nickel chloride hexahydrate and the rare earth metal compound is used to treat the crystalline zeolite is a mixture of the chlorides of at least lanthanum, cerium, praseodymium, neodymium, samarium and gadolinium.

12. The method of claim 8 wherein the platinum content of the impregnating solution is sufficient to provide a platinum content of the cation exchanged zeolite ranging from about 0.01 to about 1 percent by weight.

13. The method of claim 8 wherein the platinum content of the impregnating solution is sufficient to provide a platinum content of the cation exchanged zeolite ranging from about 0.05 to about 0.25 percent by weight.

* * * * *